United States Patent [19]

Lowery et al.

[11] Patent Number: 4,624,243

[45] Date of Patent: Nov. 25, 1986

[54] ENDOSCOPE HAVING A REUSABLE EYEPIECE AND A DISPOSABLE DISTAL SECTION

[75] Inventors: Guy R. Lowery, Mira Loma; Said S. Hilal, Laguna Niguel; Richard F. Carson, Jr., Orange; Danny L. Pastrick, Huntington Beach, all of Calif.

[73] Assignee: American Hospital Supply Corp., Deerfield, Ill.

[21] Appl. No.: 720,590

[22] Filed: Apr. 8, 1985

[51] Int. Cl.⁴ .............................................. A61B 1/06
[52] U.S. Cl. ..................................................... 128/6
[58] Field of Search .............. 128/3, 4, 5, 6, 7, 329 R, 128/303.15

[56] References Cited

U.S. PATENT DOCUMENTS

| | | | |
|---|---|---|---|
| 1,621,159 | 3/1927 | Evans | 128/6 |
| 1,624,716 | 4/1927 | Cerbo | 128/6 |
| 2,224,464 | 12/1940 | Wolf | 128/303.14 |
| 2,932,294 | 4/1960 | Fourestier et al. | 128/6 |
| 2,990,830 | 7/1961 | Hett | 128/4 |
| 3,373,736 | 3/1968 | Fiore | 128/6 |
| 3,413,067 | 11/1968 | Froio | 356/241 |
| 3,417,745 | 12/1968 | Sheldon | 128/6 |
| 3,417,746 | 12/1968 | Moore et al. | 128/6 |
| 3,643,653 | 2/1972 | Takahashi et al. | 128/6 |
| 3,709,214 | 1/1973 | Robertson | 128/4 |
| 3,804,081 | 4/1974 | Kinoshita et al. | 128/6 |
| 3,870,036 | 3/1975 | Fiore | 128/6 |
| 3,941,121 | 3/1976 | Olinger et al. | 128/6 |
| 4,072,147 | 2/1978 | Hett | 128/6 |
| 4,076,018 | 2/1978 | Heckele | 128/6 |
| 4,082,946 | 4/1978 | Heine et al. | 128/6 X |
| 4,188,942 | 2/1980 | Fehlberg | 128/6 |
| 4,215,678 | 8/1981 | Heine et al. | 128/6 |
| 4,254,762 | 3/1981 | Yoon | 128/6 |
| 4,269,192 | 5/1981 | Matsuo | 128/6 X |
| 4,279,247 | 7/1981 | Kinoshita | 128/6 |
| 4,294,234 | 10/1981 | Matsuo | 128/6 |
| 4,306,546 | 12/1981 | Heine et al. | 128/6 |
| 4,367,730 | 1/1983 | Tanaka | 128/6 |
| 4,369,768 | 1/1983 | Vukovic | 128/6 |
| 4,390,012 | 6/1983 | Mizumoto | 128/4 |
| 4,407,272 | 10/1983 | Yamaguchi | 128/6 |
| 4,411,257 | 10/1983 | Machida | 128/6 |
| 4,440,157 | 4/1984 | Shishido | 128/6 |

FOREIGN PATENT DOCUMENTS 3008502 10/1980 Fed. Rep. of Germany .......... 128/6

OTHER PUBLICATIONS

"The Thackray Arthroscope", Thackray Arthroscopy, Charles F. Thackray USA Inc., Woburn, Massachusetts.

Primary Examiner—William H. Grieb
Attorney, Agent, or Firm—Gordon L. Peterson

[57] ABSTRACT

An endoscope comprising a reusable eyepiece and a disposable distal section mounted on the eyepiece in a predetermined angular orientation so that light can be conducted from the eyepiece through the distal section and an image can be conducted from the distal section to the eyepiece. Image conduction is accomplished, in part, by a somewhat resilient, nontubular image-conducting rod. Focusing is accomplished by a focusing ring which rotates, but does not translate, on the housing. The distal section is adapted to be at least partially received within a patient and can be introduced by an introducer attached to the distal section.

28 Claims, 10 Drawing Figures

ENDOSCOPE HAVING A REUSABLE EYEPIECE AND A DISPOSABLE DISTAL SECTION

BACKGROUND OF THE INVENTION

Endoscopes are commonly used for observing, studying and/or treating internal body tissues and structure. An endoscope may include, for example, an eyepiece assembly and a distal section. The eyepiece assembly may include, for example, an objective lens, and the distal section is sized to be passed into the internal body region that is to be viewed or treated.

After each usage, it is necessary to thoroughly sterilize at least the distal section of the endoscope, and this is time consuming. It has been proposed in Heine et al U.S. Pat. No. 4,306,546 to disconnectably couple the distal section of an endoscope to a head so that the distal section can be discarded, and the head can be reused. However, this endoscope does not provide for angularly orienting the distal section relative to the head, and therefore, cannot be used if such orientation is necessary.

To enable an endoscope to be used for viewing, it is necessary to conduct light from the eyepiece assembly to the distal section and to conduct an image through the distal section to the eyepiece assembly for viewing by the physician. To enable the image to be conducted, the distal section may comprise a rigid body and lenses or a rigid image-conducting rod within the body. However, the lenses and/or the rigid image-conducting rod tend to break if the body of the distal section is distorted. Alternatively, coherently aligned optical fibers may be used for image transmission. Although the optical fibers are flexible and not likely to break, it is quite costly to obtain the necessary coherent alignment of the optical fibers so that they will transmit an image. Flexible endoscopes are known, but their flexibility limits their maneuverability within the patient.

Focusing of the optics of the endoscope can be accomplished, for example, as shown in Olinger et al U.S. Pat. No. 3,941,121 by rotating a threaded member of the eyepiece assembly in and out. However, the repeated axial advance and retraction of the threaded focusing member increases the likelihood of migration of dirt and other contaminants into the interior of the endoscope. This is unsuitable for an instrument which is to be sterile.

A common technique for introducing an endoscope is to insert a sleeve containing a pointed rod through a cut in the skin and then advancing the pointed rod to form a portion of the desired passage. The pointed rod is then removed, and a blunt rod is inserted through the sleeve to complete formation of the passage. After the blunt rod is removed, the endoscope can be inserted through the sleeve. This technique requires the use of a multiplicity of components, each of which must be resterilized prior to subsequent use. In addition, this technique may cause trauma. It is also known to introduce a probe or catheter into the vascular system by inserting a relatively large diameter needle into the vascular system and then inserting the probe or catheter through the needle. Although this technique has not, to our knowledge, been applied to endoscopes, there is no adequate way to minimize injury due to the needle following insertion.

SUMMARY OF THE INVENTION

This invention solves the problems discussed above. With this invention, a disposable distal section of an endoscope is releasably mounted on a reusable eyepiece assembly in a predetermined angular orientation so that light can be transmitted to and from the distal section. An image is transmitted from the distal section to the eyepiece assembly utilizing relatively inexpensive and non-fragile components. With this invention, focusing is accomplished by a focusing ring which does not translate, and accordingly, the likelihood of the entry of contaminants into the eyepiece assembly as a result of focusing is materially reduced. Finally, the endoscope can be introduced with an introducer which forms a part of the endoscope and which can be retracted to expose the distal end of the distal section and to minimize the likelihood of injury from the needle.

The reusable eyepiece assembly may include, for example, a housing, first light-conducting means on the housing for conducting light to a first location and second light-conducting means including a lens and a viewing port for conducting light from a second location to the viewing port. The first and second locations are located distally of the viewing port.

The disposable distal section may include, for example, an elongated body adapted to be at least partially received within a patient and having proximal and distal ends, first light-conducting means carried by the body for conducting light from a first location adjacent the proximal end of the body to adjacent the distal end of the body and second light-conducting means carried by the body for conducting light from adjacent the distal end of the body proximally to a second location.

The first locations and/or the second locations are alignable only in a predetermined angular position of the distal section and the eyepiece assembly. The distal section is releasably mounted on the eyepiece assembly in such predetermined angular orientation so that the first locations are in general alignment, and the second locations are also in general alignment. With this construction, light can be conducted between the distal section and the eyepiece assembly, and the distal section can be removed from the eyepiece assembly and discarded after use without discarding the eyepiece assembly.

It would be possible to avoid the need for the predetermined angular orientation by providing a tubular light-supplying pathway from the eyepiece assembly to the distal section. However, this would increase the cost of the endoscope. Also, a coherent image could not be transmitted if the image-transmitting portions of the light conductors were tubular.

In a preferred construction, a cooperating projection and recess on the eyepiece assembly and the distal section are used for providing the predetermined angular orientation. The projection and recess can be on the distal section and housing, respectively, or visa versa.

With this invention, fragile lenses and rigid and fragile image-conducting rods, as well as the relatively expensive, coherently aligned optical fibers for image conduction are eliminated in favor of a somewhat resilient, nontubular, elongated image-conducting rod at least partially in the body of the distal section. The flexibility of the rod and of the body of the distal section should be sufficient to significantly reduce the likelihood of breakage, but the rod and body should be rigid enough to permit complete maneuverability of the distal section within the patient. An image-conducting rod of this type may be constructed, for example, from a fused bundle of optical fibers, and this can be accomplished relatively inexpensively. A tubular rod is not used because it could not conduct a full image. Only a single rod of this type is required to conduct an image.

Focusing is accomplished by a focusing ring mounted for rotation without translation and means responsive to the rotation of the focusing ring to provide focusing. More specifically, the endoscope includes light-conducting means, which in turn includes a lens in the housing of the eyepiece assembly and an elongated light conductor at least partially in the body. Turning of the focusing ring brings about adjustment in the relative axial position of the lens and the proximal end of this light conductor.

The introducer features of this invention are specifically applicable to an endoscope, but more generally applicable to a probe assembly. The introducer can advantageously include a hub and a tubular sheath having a sharp distal end adapted to penetrate tissue, a proximal end, a longitudinal passage extending through the sheath from the proximal end to the distal end and opening at the distal end. The hub is mounted on the sheath adjacent the proximal end of the sheath. A probe, such as the distal section of an endoscope, is provided with a hub, and the two hubs can be coupled together for relative movement. This mounts the introducer so that it forms a part of the probe. This also enables the introducer to be moved from an extended position in which it essentially covers the distal end of the body of the probe to a retracted position in which the distal end of the body of the probe projects out of the distal opening of the sheath. With this arrangement, the needle can be used to penetrate tissue and thereafter be withdrawn to expose the distal end of the body of the probe. This tends to protect the patient from injury due to the sharp distal end of the sheath even when the probe is maneuvered in the patient. The distal section and the introducer are disposable and, therefore, resterilization is eliminated.

The features of this invention are applicable to endoscopes generally and, in particular, to an endoscope for orthopedic use. Although the features of this invention are particularly adapted for use together, they may be used singly or in any combination.

The invention, together with additional features and advantages thereof, may best be understood by reference to the following description taken in connection with the accompanying illustrative drawing.

DESCRIPTION OF THE PREFERRED EMBODIMENTS

Figure 1:
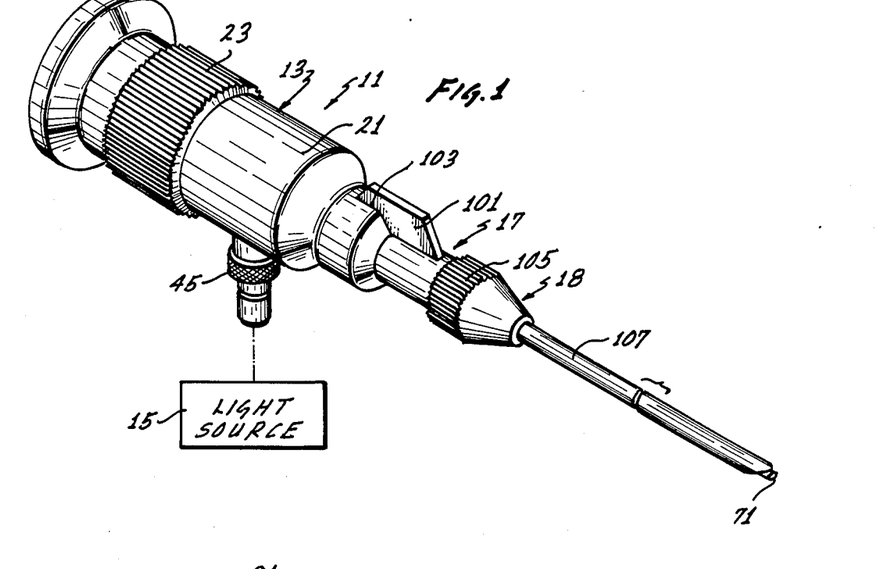
FIG. 1 is an isometric view of one form of endoscope constructed in accordance with the teachings of this invention.

FIG. 1 shows an endoscope 11 which generally comprises a reusable eyepiece assembly 13 coupled to a suitable light source 15, a disposable distal section 17 and an introducer 18. The eyepiece assembly 13 (FIGS. 1–3) includes a housing 19 which includes tubular housing sections 21 and 23, a mounting section 25 (FIG. 2) having a bore 27 extending therethrough, a lens bushing 29 threaded into a counterbore 31 of the mounting section 25, an objective lens 33 carried by the lens bushing 29, a tubular coupling 35 and a plano lens 37 at a viewing port 39.

The housing section 21, which may be constructed of metal, has an axial passage 41 extending completely through it and a reduced-diameter nose 43 at its distal end. The mounting section 25 is threaded within the passage 41, and a coupling 45 is suitably attached to the peripheral wall of the housing 21 for coupling light-conducting means in the form of a fused or flexible light-conducting rod 47 to the housing 19. The rod 47 terminates in a distal end 49 at a first location.

The housing section 23 (FIG. 2), which may be constructed of a plastic material, is suitably mounted on the housing section 21 for rotation without translation. Although this can be accomplished in different ways, in this embodiment, set screws 51 carried by the housing section 23 ride in an annular groove 53 formed in the outer surface of the housing section 21. The interface between the housing sections 21 and 23 is sealed by a seal 55.

The plano lens 37 is retained between an annular flange 57 of the housing section 23 and the coupling 35 which is threaded into the housing section 23. The coupling 35 has a skirt 59 with keys 61 which are received in keyways 63, respectively, formed on the lens bushing 29. The lens bushing 29, the mounting section 25 and the coupling 35 may be constructed of metal.

With this construction, rotation of the housing section 23 relative to the housing section 21 rotates the coupling 35 which, in turn, rotates the lens bushing 29 and the lens 33 to thread the lens bushing 29 further into, or out of, the counterbore 31. In either event, the axial position of the lens 33 is adjusted as a result of rotation of the housing section 23. In this manner, the housing section 23 functions as a focusing ring.

An image can be directed through a passage 65 which extends through the lens bushing 29 and the coupling 35, the lens 33 and the plano lens 37 to the viewing port 39. In this embodiment, this light-conducting means may be considered as terminating at a second location in the vicinity of the proximal end of the bore 27.

Figure 3:
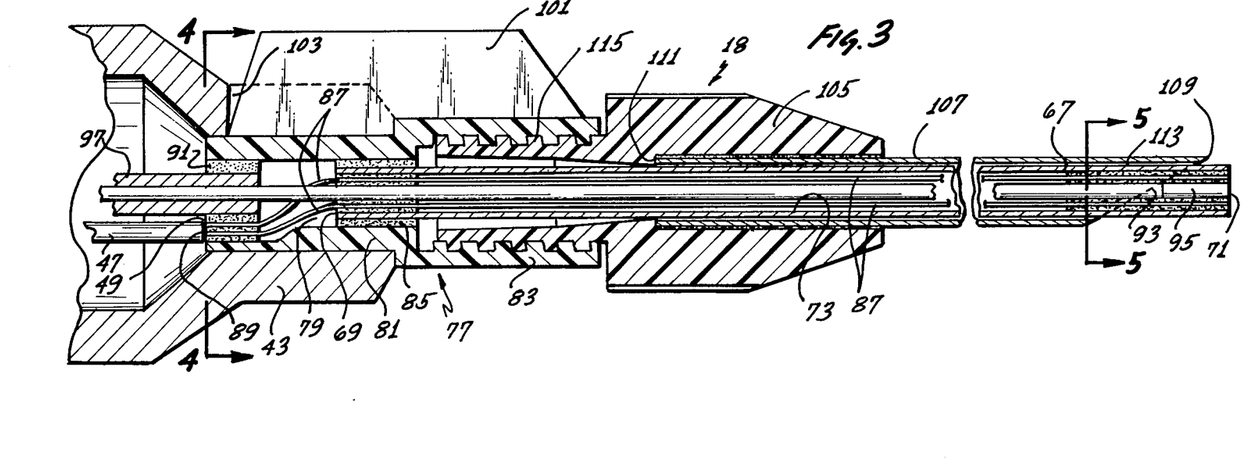
FIG. 3 is an enlarged, fragmentary, sectional view taken on an axial plane through the endoscope and illustrating a distal region of the eyepiece assembly, the introducer, and the distal section. The introducer is in the retracted position.
Figure 4:
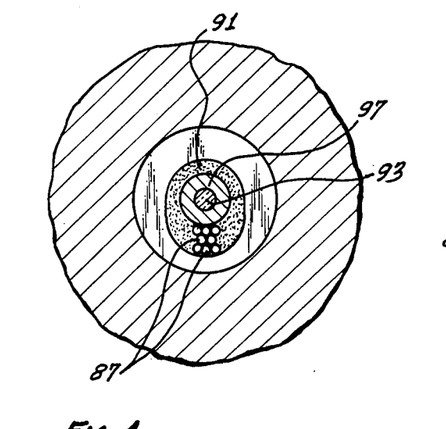
FIGS. 4 and 5 are enlarged sectional views taken generally along lines 4—4 and 5—5, respectively, of FIG. 3.
Figure 5:
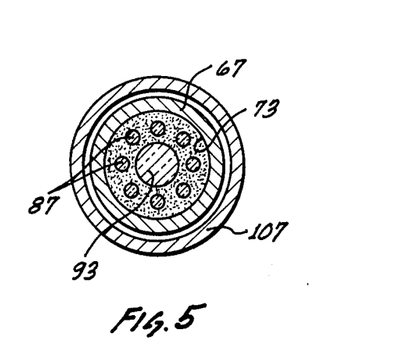
Figure 6:
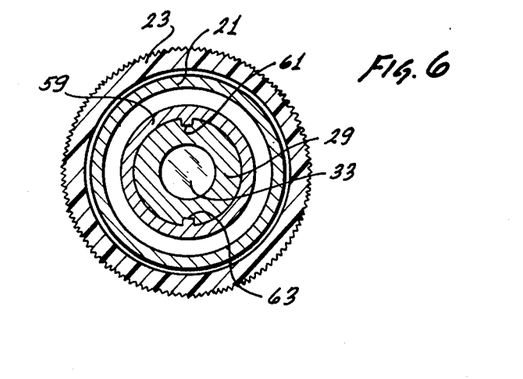
FIG. 6 is an enlarged sectional view taken generally along lines 6—6 of FIG. 2.

The distal section 17 includes an elongated body 67 (FIG. 3) of stainless steel or other suitable metal which is at least somewhat resiliently bendable and is sized and adapted to be at least partially received within a patient. The body 67 has a proximal end 69 (FIG. 3), an open distal end 71 and an axial passage 73 (FIGS. 3 and 5)

which, in this embodiment, extends from the proximal end 69 completely through the body 67 to the distal end 71. The distal section 17 also includes a hub 77 of a plastic material having an axial passage 79 extending completely through it, a small diameter section 81 and a large diameter section 83 (FIG. 3). A region of the hub 77 extends proximally of the body 67 and forms a body extension which may be considered as a portion of the body 67. A proximal region of the body 67 is bonded to a region of the small diameter section 81 by bonding material 85, and the large diameter section 83 is spaced radially from the body 67.

The distal section 17 also includes light-conducting means for conducting light to the distal end 71 of the body 67, and second light-conducting means for conducting an image from adjacent the distal end 71 proximally. Although various constructions can be employed, in the embodiment illustrated, light-conducting means in the form of optical fibers 87 extend from their proximal ends 89 at a first location near the proximal end of the hub 77 substantially to the end wall 75. Near the proximal end of the hub 77, the optical fibers 87 are collected in a bundle, held together and mounted on the hub by potting 91. Additional potting may be used near the distal end 71 (FIG. 3) to retain the optical fibers 87 in position.

To conduct an image from the distal end 71 proximally, a nontubular, solid image-conducting rod 93 and the usual distal lens 95 affixed to the rod 93 are employed. The rod 93 is in the form of a fused bundle of optical fibers with an appropriate coating to provide some resilience so that it can be deflected somewhat without fracturing. Image-conducting rods of this type are known per se, but to our knowledge, have not been applied heretofore in an endoscope. The rod 93 in the illustrated embodiment is a solid, nontubular cylinder which extends from the lens 95 proximally through the passage 73 of the body 67 and through a sleeve 97 which is received in the bore 27 of the mounting section 25. The rod 93 terminates in a proximal end 99 at a second location which is flush with the proximal end of the sleeve 97. The rod 93 is coaxial with the body 67, the lenses 33 and 37 and the viewing port 39.

The sleeve 97 is received within the proximal end of the hub 77 and is retained therein by the potting 91. The sleeve 97 protects the proximal regions of the rod 93 during assembly of the distal section onto the eyepiece assembly 13 and accurately aligns the rod so that it is coaxial with the lenses 33 and 37.

Figure 2:
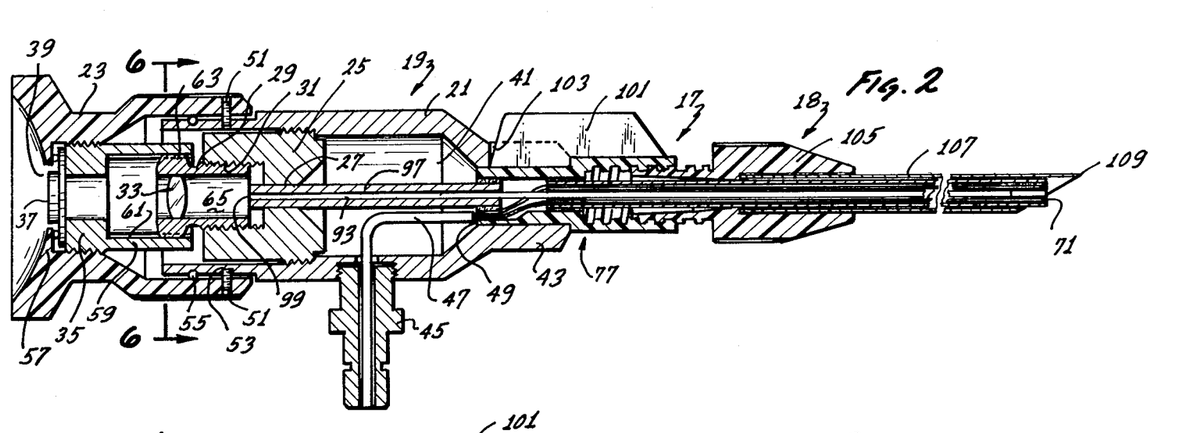
FIG. 2 is a longitudinal, sectional view taken on an axial plane through the endoscope, with the introducer extended.

The distal section 17 is removably mounted on the eyepiece assembly 13 in a predetermined angular orientation so that the rod 93 is coaxial with the lenses 33 and 37, and the distal end 49 of the rod 47 is in alignment with the proximal ends 89 of the optical fibers 87 as shown on FIG. 2. Although this can be accomplished in different ways, in the embodiment illustrated, the nose 43 of the eyepiece assembly 13 receives the small diameter section 81 of the hub 77 with a friction fit as shown in FIGS. 2 and 3. Angular orientation is provided by a cooperating projection in the form of a fin 101 on the hub 77 and a recess in the form of a slot 103 in the nose 43. Because the distal end 49 of the rod 47 and the proximal ends 89 of optical fibers 87 are spaced radially from the axis of the endoscope 11 and are not annular, it is necessary to mount the distal section on the eyepiece assembly in the predetermined angular orientation. Focusing is accomplished by relatively adjusting the relative axial position of the lens 33 and the proximal end 99 of the image-conducting rod 93. As explained above, rotation of the housing section 23, which forms a focusing ring, moves the lens 33 axially along the optical axis of the endoscope 11 to thereby move the lens relative to the proximal end 99 of the rod.

The introducer 18 includes a hub 105 (FIGS. 1-3) of a suitable plastic and a tubular sheath 107 of metal. The sheath 107 has a sharp, distal end 109 adapted to penetrate tissue, a proximal end 111 (FIG. 3) and a longitudinal passage 113 extending through the sheath from the proximal end of the sheath to the distal end of the sheath and opening at the distal end of the sheath. A proximal region of the sheath 107 is received within the hub 105 and suitably retained therein as by bonding or an adhesive.

The outside diameter of the sheath 107 is small enough to be used in needle-like fashion to penetrate tissue, and the passage 113 is of large enough diameter to slidably receive the body 67. The hub 105 has an externally threaded reduced-diameter section 115 which can be threaded into the large diameter section 83 of the hub 77 to mount the introducer 20 on the distal section 17.

Figure 7:
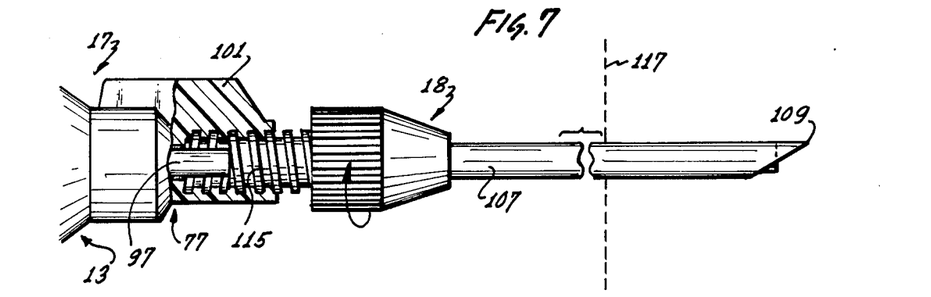
FIGS. 7 and 8 are elevational views partially in section of essentially the same region of the endoscope shown in FIG. 3 and illustrating the introducer in the extended and retracted positions, respectively.
Figure 8:
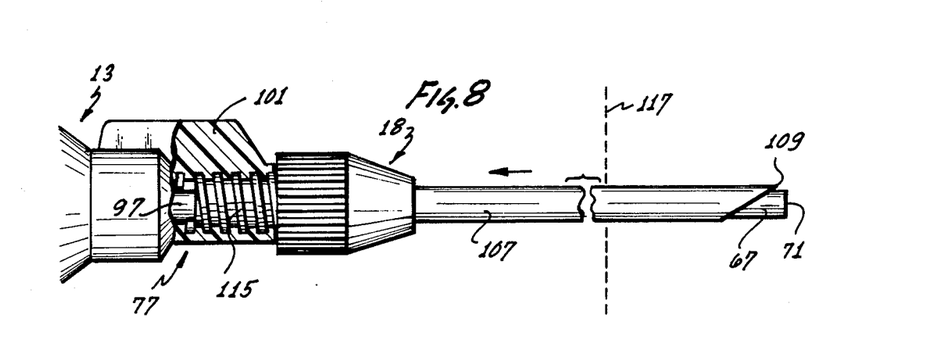

The use of the endoscope 11 is illustrated by way of example in FIGS. 7 and 8. Although the endoscope 11 may have different uses, it is particularly adapted for direct visualization and diagnosis of disorders of the orthopedic system, such as within the knee.

With the introducer 18 partially threaded into the hub 77 of the distal section 17 as shown in FIG. 7, the introducer is in the extended position and may essentially cover the distal end 71 of the body 67 as shown in FIG. 7 or fully cover the distal end 71. With the endoscope 11 in the position of FIG. 7, the introducer 18 is introduced directly into the knee 117. When the desired position has been reached, the introducer 18 is rotated to thread the reduced diameter section 115 farther into the hub 77 to thereby move the introducer 18 to the retracted position in which the distal end 71 and an adjacent distal region of the body 67 lie outside of the sheath 107 and are exposed as shown in FIG. 8. This tends to protect the patient from injury due to the sharp distal end 109 of the sheath 107 even when the distal section 17 is maneuvered within the knee.

Illumination is provided from the light source 15 through the light-conducting rod 47 and the optical fibers 87 to the distal end 71 of the body 67. An image is conducted via the lens 95, the image-conducting rod 93 and the lenses 33 and 37 to the viewing port 39 to thereby permit observation of the image by the physician. Focusing can be accomplished as described above by rotation of the housing section 23 to move the lens 33 axially relative to the proximal end 99 of the image-conducting rod 93.

Following introduction into the knee and retraction of the introducer 18, the endoscope 11, and in particular, the body 67, can be moved within the knee to enable the physician to view the desired region of the knee. The body 67 and the rod 93 are somewhat resilient to thereby minimize the likelihood of fracture of the rod 93 but sufficiently rigid to allow the desired movement of the body 67 within the knee.

Figure 9:
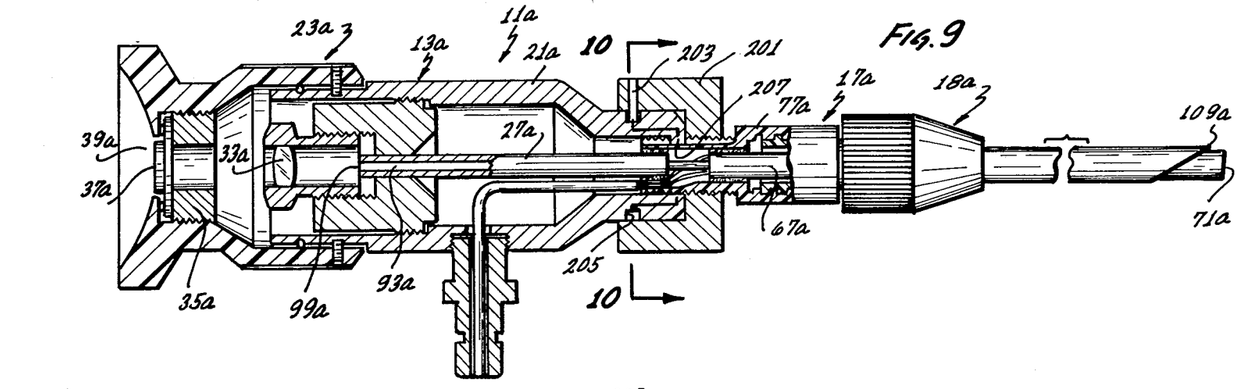
FIG. 9 is a sectional view taken on an axial plane through a second form of endoscope constructed in accordance with the teachings of this invention.
Figure 10:
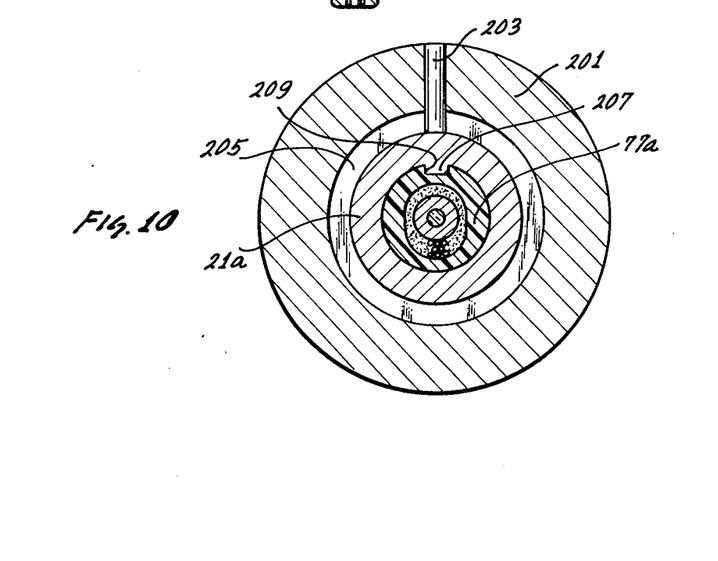
FIG. 10 is an enlarged, sectional view taken generally along line 10—10 of FIG. 9.

FIGS. 9 and 10 show an endoscope 11a which is identical to the endoscope 11 in all respects not shown or described herein. Portions of the endoscope 11a corresponding to portions of the endoscope 11 are designated by corresponding reference numerals followed by the letter "a."

The primary difference between the endoscopes 11 and 11a is the manner in which they accomplish focusing. In both embodiments, rotation of a focusing ring brings about adjustment in the relative axial position of the lens and the proximal end of the image-conducting rod. However, in the embodiment of FIGS. 9 and 10, the lens 33a is stationary, and the image-conducting rod 93a moves axially relative to the lens.

More specifically, the eyepiece assembly 13a includes a housing section 201 in the form of a focusing ring which is mounted on the housing section 21a for rotation without translation by set screws 203 which are received within an annular groove 205 of the housing section 21a. The hub 77a is threaded into the housing section 201 and is held against rotation by a key 207 on the housing section 21a and a cooperating keyway 209 formed in the hub. Accordingly, rotation of the housing section 201 causes the hub 77a and the entire distal section 17a, as well as the introducer 18a, to translate. This moves the proximal end 99a of the image-conducting rod 93a axially relative to the stationary lens 33a. Because the lens 33a is stationary, the coupling 35a has no skirt 59, and the housing section 23a does not function as a focusing ring.

Although exemplary embodiments of the invention have been shown and described, many changes, modifications and substitutions may be made by one having ordinary skill in the art without necessarily departing from the spirit and scope of this invention.

We claim:

1. An endoscope comprising:
   a reusable eyepiece assembly including a housing, first light-conducting means on the housing for conducting light to a first location and a second light-conducting means including a lens and a viewing port for conducting light from a second location to the viewing port, said first and second locations being located distally of the viewing port;
   a disposable distal section including an elongated body adapted to be at least partially received within a patient and having proximal and distal ends, first light-conducting means carried by the body for conducting light from a first location distally to adjacent the distal end of the body and second light-conducting means carried by the body for conducting light from adjacent the distal end of the body proximally to a second location;
   each of said first light-conducting means terminating substantially at the associated first locations and each of said seond light-conducting means terminating substantially at the associated second locations;
   at least one of said first locations and said second locations being alignable only in a predetermined angular position of the distal section and the eyepiece assembly; and
   means for releasably mounting the distal section on the eyepiece assembly in said predetermined angular orientation so that said first locations are in general alignment and said second locations are in general alignment whereby light can be conducted between the distal section and the eyepiece assembly and the distal section can be removed from the eyepiece assembly and discarded after use without discarding the eyepiece assembly.

2. An endoscope as defined in claim 1 wherein Isaid mounting means includes a cooperating projection and recess on the eyepiece assembly and the distal section for providing said predetermined angular orientation.

3. An endoscope as defined in claim 2 wherein said projection includes a fin on the body and a slot on the housing of the eyepiece.

4. An endoscope as defined in claim 2 wherein said mounting means includes a nut rotatably mounted on the eyepiece housing and cooperating screw threads on the nut and body of the distal section, and said projection and recess are on the nut and distal section.

5. An endoscope as defined in claim 1 wherein said second light-conducting means on the body of the distal section includes a somewhat resilient, non-tubular elongated image conducting rod at least partially in said body and said body is at least somewhat resilient.

6. An endoscope as defined in claim 1 wherein said second light-conducting means of said eyepiece assembly includes a lens and said second light-conducting means on the body includes an elongated light conductor at least partially in said body and having a proximal end lying proximally of the lens, and said endoscope includes focusing means for relatively adjusting the relative axial position of the lens and said proximal end of the elongated light conductor, said focusing means includes a focusing ring, means for mounting the focusing ring for rotation without translation and means responsive to the rotation of the focusing ring to adjust the relative axial position of the lens and the proximal end of the light conductor.

7. An endoscope as defined in claim 6 wherein said second light-conducting means on the body of the distal section includes a somewhat resilient, non-tubular elongated image conducting rod at least partially in said body and said body is at least somewhat resilient.

8. An endoscope as defined in claim 1 including an introducer which includes a hub and a tubular sheath having a sharp distal end adapted to penetrate tissue, a proximal end and a longitudinal passage extending through said sheath from the proximal end of the sheath to the distal end of the sheath and opening at the distal end of the sheath, said hub being mounted on the sheath adjacent the proximal end of the sheath, said distal section includes a hub mounted on a proximal region of the body and the body is receivable in the passage of the sheath, and said endoscope includes means for coupling the hubs together for relative movement so that the introducer can be moved from an extended position in which it essentially covers the distal end of the body to a retracted position in which the distal end of the body projects out of the distal opening of the sheath whereby the introducer can be used to penetrate tissue and thereafter be withdrawn sufficiently to expose the distal end of the body of the probe.

9. An endoscope as defined in claim 8 wherein said second light-conducting means on the body of the distal section includes a somewhat resilient, non-tubular elongated image conducting rod at least partially in said body and said body is at least somewhat resilient.

10. An endoscope as defined in claim 8 wherein said second light-conducting means of said eyepiece assembly includes a lens and said second light-conducting means on the body includes an elongated light conductor at least partially in said body and having a proximal end lying proximally of the lens, and said endoscope includes focusing means for relatively adjusting the relative axial position of the lens and said proximal end of the elongated light conductor, said focusing means includes a focusing ring, means for mounting the focusing ring for rotation without translation and means responsive to the rotation of the focusing ring to adjust the relative axial position of the lens and the proximal end of the light conductor.

11. An endoscope as defined in claim 1 wherein said mounting means includes means for guiding the distal section and the eyepiece assembly together in said predetermined angular orientation.

12. An endoscope comprising:
an eyepiece assembly including a viewing port;
a distal section including an elongated somewhat resilient body adapted to be at least partially received within a patient, said distal section having a distal end;
means for attaching the distal section to the eyepiece assembly with the distal section extending distally of the eyepiece;
light-conducting means for conducting light from adjacent the eyepiece assembly to adjacent the distal end of the body;
image-conducting means for conducting an image from adjacent the distal end of the body to the viewing port; and
said image-conducting means including a somewhat resilient nontubular elongated image-conducting rod at least partially in said body.

13. An endoscope as defined in claim 12 wherein said rod includes a fused bundle of optical fibers.

14. An endoscope as defined in claim 12 wherein at least a portion of the image-conducting rod is in the body and the light-conducting means includes optical fibers arranged in a generally tubular configuration around the image-conducting rod in said body.

15. An endoscope as defined in claim 12 wherein the image-conducting means has only one of said rods.

16. An endoscope as defined in claim 12 wherein the image-conducting rod projects proximally of the body and said endoscope includes an elongated sleeve on at least a region of the rod which is proximal to the body.

17. An endoscope as defined in claim 16 wherein the eyepiece assembly includes a housing and a tubular mounting section in said housing which receives at least part of the sleeve.

18. An endoscope comprising:
an eyepiece assembly including a housing having a viewing port;
a distal section including an elongated body adapted to be at least partially received within a patient, said body having a distal end;
first light-conducting means for conducting light from adjacent the housing to adjacent the distal end of the body;
second light-conducting means for conducting light from adjacent the distal end of the body to the viewing port, said second light-conducting means including a lens in said housing and an elongated light conductor at least partially in said body and having a proximal end lying distally of the lens;
focusing means for relatively adjusting the relative axial position of the lens and the proximal end of the light conductor;
said focusing means including a focusing ring, means for mounting the focusing ring for rotation without translation and means responsive to rotation of the focusing ring to adjust the relative axial position of the lens and the proximal end of the light conductor;

the light conductor being movable axially with the body, said focusing means including means for threadedly coupling the focusing ring and the body and means for holding the body against rotation whereby rotation of the focusing ring moves the body and the light conductor to adjust the relative axial position of the lens and the light conductor.

19. An endoscope as defined in claim 18 wherein said second light-conducting means includes a somewhat resilient, non-tubular elongated image conducting rod at least partially in said body and said body is at least somewhat resilient.

20. A probe assembly comprising:
an introducer including a hub and a tubular sheath having a sharp distal end adapted to penetrate tissue, a proximal end, a longitudinal passage extending through the sheath from the proximal end to the distal end and opening at said distal end, said hub being mounted on the sheath adjacent the proximal end of the sheath;
a probe including an elongated body having a distal end and sized to be movable in said passage of said sheath and a hub mounted on a proximal region of the body, said body being receivable in said passage with said hubs being adjacent the proximal end of said sheath;
means for coupling said hubs together for relative movement so that the introducer can be moved from an extended position in which it essentially covers the distal end of the body to a retracted position in which the distal end of the body projects out of the distal opening of the sheath whereby the introducer can be used to penetrate tissue and thereafter be withdrawn sufficiently to expose the distal end of the body of the probe; and
said coupling means including means for positively retaining said introducer in at least one of said positions against a force urging the introducer toward the other of said positions.

21. A probe assembly as defined in claim 20 wherein said coupling means includes means responsive to relative rotation between the hubs for moving the introducer from the extended position to the retracted position.

22. A probe assembly as defined in claim 20 wherein said coupling means includes screw threads on said hub.

23. A probe assembly as defined in claim 20 wherein said probe is an endoscope and includes light-conducting means for conducting light in both directions longitudinally of the body.

24. A probe assembly as defined in claim 23 wherein said light-conducting means includes a somewhat resilient, non-tubular elongated image conducting rod at least partially in said body and said body is at least somewhat resilient.

25. A probe assembly as defined in claim 23 wherein said light-conducting means includes a lens and an elongated light conductor at least partially in said body and having a proximal end lying proximally of the lens, and said endoscope includes focusing means for relatively adjusting the relative axial position of the lens and said proximal end of the elongated light conductor, said focusing means includes a focusing ring, means for mounting the focusing ring for rotation without translation and means responsive to the rotation of the focusing ring to adjust the relative axial position of the lens and the proximal end of the light conductor.

26. A probe assembly as defined in claim 25 wherein said light-conducting means includes a somewhat resilient, non-tubular elongated image conducting rod at least partially in said body and said body is at least somewhat resilient.

27. A probe assembly as defined in claim 20 wherein the retaining means positively retains the introducer in each of said positions against a force urging the introducer toward the other of said positions.

28. An endoscope comprising:
an eyepiece assembly including a housing having a viewing port;
a distal section including an elongated body adapted to be at least partially received within a patient, said body having a distal end;
first light-conducting means for conducting light from the housing to adjacent the distal end of the body;
second light-conducting means for conducting light from adjacent the distal end of the body to the viewing port, said second light-conducting means including a lens in said housing and an elongated light conductor at least partially in said body and having a proximal end lying distally of the lens;
focusing means for relatively adjusting the relative axial position of the lens and the proximal end of the light conductor;
said focusing means including a focusing ring, said focusing ring being part of said housing and carrying a viewing port, means for mounting the focusing ring for rotation without translation and means responsive to rotation of the focusing ring to adjust the relative axial position of the lens and the proximal end of the light conductor; and
said focusing means including means for mounting the lens on the housing for rotation and translation and means for drivingly coupling the focusing ring and the lens so that the focusing ring can rotate and translate the lens to adjust the axial position of the lens relative to the proximal end of the light conductor.

* * * * *